United States Patent [19]

Speigel

[11] Patent Number: 5,823,932

[45] Date of Patent: Oct. 20, 1998

[54] APPARATUS AND METHOD FOR MODIFYING HUMAN BEHAVIOR BY TRIGGERING POSITIVE AND AVERSIVE POST-HYPNOTIC SUGGESTIONS

[75] Inventor: Robert B. Speigel, Mercer Island, Wash.

[73] Assignee: ProGenesis Incorporated, Mercer Island, Wash.

[21] Appl. No.: 771,344

[22] Filed: Dec. 16, 1996

[51] Int. Cl.[6] ................................................. A61M 21/00
[52] U.S. Cl. ............................... 600/26; 600/27; 600/28
[58] Field of Search ................. 600/26–28; 128/897–899

[56] References Cited

U.S. PATENT DOCUMENTS 5,425,699   6/1995   Speigel .

*Primary Examiner*—Jennifer Bahr
*Assistant Examiner*—Rosiland Kearney
*Attorney, Agent, or Firm*—Christensen O'Connor Johnson & Kindness PLLC

[57] ABSTRACT

An apparatus (10) for modifying undesired behaviors in humans who have undergone one or more hypnotherapy sessions to implant positive and aversive posthypnotic suggestions which are to be elicited in response to corresponding detected trigger events. In a preferred embodiment, the apparatus is a watch (30) and includes signal generators (15, 16, 19, 20) which are controlled by a processor (12) to generate tactile, visual and/or audio active signals that trigger positive and aversive posthypnotic suggestions. The apparatus is programmed to randomly generate a plurality of positive active signals during a period of time programmed by the subject. Additionally, manual controls (14, 18) are provided to allow the subject to selectively activate the positive active signals or negative active signals as needed.

29 Claims, 7 Drawing Sheets

APPARATUS AND METHOD FOR MODIFYING HUMAN BEHAVIOR BY TRIGGERING POSITIVE AND AVERSIVE POST-HYPNOTIC SUGGESTIONS

FIELD OF THE INVENTION

The present invention relates to an apparatus for modifying human behavior by triggering positive and aversive post-hypnotic suggestions elicited by active signals.

BACKGROUND OF THE INVENTION

Clinical hypnotherapy is used to treat a wide variety of psychological problems. The process of clinical hypnotherapy involves helping a patient achieve a very relaxed state and heightened state of suggestibility so that he/she will accept, on a subconscious level, ideas, beliefs or suggestions to which the patient might not otherwise be receptive. The patient's lack of receptivity may be due to stress, tension or certain preconceived ideas. However, the purpose of these suggestions is to disrupt the logic/thought pattern which has created the specific psychological problem.

For example, hypnotherapy may be used to treat people who suffer from extreme test anxiety. Typically, test anxiety results in the patient not fully performing up to his/her capabilities in test taking situations. A typical logic/thought pattern for such a person may be as follows: "If I do badly on the test then I will get a bad grade in the course-then I won't get into college-then I won't become a doctor then I will be a total failure in life." In the patient's mind, the perceived consequences of performing poorly on the test are tremendous. The resulting anxiety from this logic/thought pattern may actually result in the patient performing substantially below his/her capabilities.

Hypnotherapy involves three separate phases, these being (i) a relaxation phase, (ii) a suggestion phase, and (iii) a post-hypnotic suggestion phase. The process begins with the relaxation phase whereby the therapist helps the patient become more comfortable and relaxed in order for the patient to be receptive to the therapist's suggestions. Once the patient has reached a sufficient level of relaxation, the therapist provides suggestions which are specifically intended to reduce the patient's symptoms. It is the purpose of the hypnotherapy to integrate these suggestions into the patient's subconscious mind so that the suggestions become urges to take a specified action or actions. The therapist will then include one or more suggestions intended to occur after the patient is removed from his/her state of deep relaxation or hypnosis. This set of suggestions are known as "post-hypnotic" suggestions. While they are provided to the patient in the hypnotic state, they are intended to be "cued" by stimuli which will occur later when the patient is no longer in the hypnotic state. That is, the patient is instructed (while in the hypnotic state) to experience the full strength of the post-hypnotic suggestion each time he/she later experiences a specific cue, such as a feeling of anxiety in anticipation of in upcoming test.

For example, the therapist might suggest to the patient (while the patient is in the hypnotic state) that any time he/she experiences anxiety about an upcoming test, to remember and experience the same feelings of relaxation as he/she is feeling while under hypnosis. In this case the post-hypnotic suggestion is "relaxation" which is to be triggered by an internal feeling (cue) of anxiety about an upcoming test (stimulus). Thus, the post-hypnotic suggestions recall the feelings of deep relaxation experienced during hypnosis and the patient "re-experiences" these relaxed feelings thereby disrupting his/her anxiety about the upcoming test situation.

Typically, hypnotherapy sessions are conducted by an experienced therapist who is actually present with the patient. In a formal hypnotherapy session for alleviating such problems as smoking, the therapist will develop a post-hypnotic suggestion which may be unique for the patient. The suggestion may trigger positive feelings or negative, aversive feelings. For example, an aversive post-hypnotic suggestion might be that when the patient pulls a cigarette from a cigarette pack, the cigarette will begin to get hotter and hotter between his fingers (the negative suggestion) until he is forced to drop it to keep from being burned. Other suggestions might work better for other patients. For example, the therapist might suggest that the cigarette turns into a wiggling, slimy worm when it is pulled from the cigarette pack. The pack itself could be targeted for a post-hypnotic suggestion. Thus, it might be suggested that when purchasing cigarettes (the cue), the patient will begin to feel nauseous and dizzy (the post-hypnotic suggestion) and should go out into the street for fresh air.

Suggestions such as these are also used as aids in treatments other than hypnotherapy through the use of vivid images to achieve a desired outcome. For example, non-hypnotic imaging is used in conjunction with radiation and chemotherapy by oncology personnel. The patient usually is told to imagine himself (or a powerful surrogate) "sailing" through the bloodstream, finding and battling the cancer, and finally overcoming it. A patient might imagine herself finding the cancer as a huge knot of gnarled roots blocking her way. She would image that she obtained a small ax and laboriously severed each root, working persistently until the cancer could take no more nourishment from her. As she would cut the roots, they would wither, and finally, the cancer itself would die when all its roots were destroyed.

The current use of formal post-hypnotic suggestion or non-hypnotic heightened suggestibility (including imaging) has been used by mental health or medical professionals who directly (or indirectly through the use of audio-tapes) aid the patient by creating the state of heightened suggestibility and then place the post-hypnotic suggestion. Although suggestion and imaging might be used even in non-therapeutic environments such as sales motivation sessions, the state of heightened suggestibility and the suggestion placement are often controlled by a human session leader or might be delivered through a pre-recorded audio-cassette program.

In the foregoing conventional methods of placing and maintaining post-hypnotic suggestions, the therapist helps create the relaxed state of heightened awareness, places the post-hypnotic suggestion, and then terminates the hypnosis. Afterward, it is intended that a recognized cue elicit the post-hypnotic suggestion from the patient's subconscious and the suggested behavior results, e.g. relaxation.

A significant problem with these conventional hypnotherapy processes is that post-hypnotic suggestions work well with some types of cues but not with others. Typically, the term "cue" means anything which is intended to elicit a post-hypnotic suggestion. For example, in the case of the post-hypnotic suggestion that a cigarette will start to get hotter and hotter when it is pulled from the cigarette pack and start to burn the smoker's fingers unless it is dropped, the cue might be when the patient reaches for his pack and feels a cigarette placed between his fingers. However, this type of cue is defined herein as an "external passive cue". That is, this cue, although located in the patient's external environment, relies upon the patient's ability to make the suggested connection between the action of taking a cigarette from an ordinary pack of cigarettes and the heating up of the cigarette so that it burns the patient's fingers. There is nothing different or unusual about the pack of cigarettes to aid the smoker's subconscious mind in making the connection between the cigarette pack and the burning fingers. Furthermore, this particular cue is "object specific". That is, it depends upon the patient obtaining his/her next cigarette from a pack of cigarettes. For example, during a weak moment the patient could consciously bypass this cue (to avoid the unwanted consequences of "burning" fingers) by having his/her spouse or friend pull the cigarette from the pack and place it between his lips.

Another problem with the foregoing conventional hypnotherapy processes is that many of them depend upon the patient awareness of his/her "internal cues". For example, a post-hypnotic suggestion to relax when a patient is feeling anxious about an upcoming test requires the patient to cue on a particular internal state. However, the patient may not be able to recognize his/her internal state at the time. That is, internal cues are not as vivid or well defined as even external passive cues, and may be particularly inaccessible to patients that exhibit certain types of behavioral disorders. In fact, many individuals are normally insensitive to a whole host of internal states such as their internal level of anxiety.

Furthermore, these conventional hypnotherapy processes put the entire responsibility for maintaining the forward progress of the treatment with the patient, who is often the weakest link. This is a particular problem when the patient experiences anxiety or is distracted during the unwanted behavior. It is known that when the patient is in a state of anxiety, he/she is even less likely to initiate the proper steps to trigger the post-hypnotic suggestion.

Also, in terms of overall treatment effectiveness, the patient must remember to reinitiate the original hypnotherapy process each time he/she wants reinforcement of the suggestion. Thus, it is easy for a patient to drift away from the treatment regimen, especially with particularly intractable disorders such as cigarette smoking, alcohol abuse and overeating. It is also known that the post-hypnotic suggestion will degrade over time. That is, the overall strength of the post-hypnotic suggestion's ability to reduce the targeted symptoms will diminish in proportion to the length of time between the placement of the post-hypnotic suggestion and the occurrence of the cue.

U.S. Pat. No. 5,425,699, issued to the present inventor, teaches a method of modifying human behavior by using automatically generated active signals ("triggers") to elicit post-hypnotic suggestions. A subject is placed in a hypnotic state, and while in that state, post-hypnotic suggestions are linked to the active signal. After the hypnotic state is terminated, the active trigger is automatically generated by an off-the-shelf wristwatch unit capable of displaying user-entered messages, such as the "Telememo 30" manufactured by Casio, Ltd. of London, England. The generating of the active message elicits the post-hypnotic suggestion, thereby modifying the subject's behavior.

While the method and apparatus disclosed in U.S. Pat. No. 5,425,699 is effective at reducing time dependent diminishment of post-hypnotic suggestions, it is somewhat limited in that it generates only a single type of active trigger, such as for a positive post-hypnotic suggestion, and generates the trigger only at preprogrammed, and therefore predictable, times of day. Thus, the active signal may not be generated at times when the subject actually most is in need of reinforcement, and the effectiveness of the active signal trigger may be reduced due to the predictability of the time of day at which it is generated.

SUMMARY OF THE INVENTION

The present invention pertains to an apparatus for treating a behavioral problem of a human subject who has undergone hypnotherapy to implant positive and aversive post-hypnotic suggestions. Features of the inventive apparatus include active signal generators for generating triggers for the positive and aversive posthypnotic suggestions in the subject, a processor for the overall control of the apparatus and for automatically programming random times to generate the positive trigger, and manual controls which allow the subject to activate either the positive or negative triggers when needed. An additional feature of the inventive apparatus is programmability which allows the subject to set a time period during which to randomly activate the positive trigger.

Typically, a subject will enter into the apparatus a normal "work day" during which positive post-hypnotic suggestions are desired. Then the processor will program a number of random times during the work day at which to activate an active signal for triggering a positive post-hypnotic suggestion.

The manual controls in the inventive apparatus allow a subject to manually activate a trigger for either a positive or an aversive post-hypnotic suggestion as needed. A preferred embodiment of the apparatus also involves the generation of redundant active triggers. Thus, a combination of one or more visual, audio or tactile triggers may be concurrently generated to trigger the positive or aversive post-hypnotic suggestions.

In a still further aspect of the present invention, a method of treating behavioral problems in a subject who has undergone one or more hypnotherapy sessions to implant positive and aversive post-hypnotic suggestion is provided. The subject is outfitted with a portable device which is capable of generating a first active signal to trigger the positive post-hypnotic suggestions in the subject, and a second active signal to trigger the aversive post-hypnotic suggestions in the subject.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention provides a method and apparatus for use in modifying human behavior through post-hypnotic suggestions. The apparatus is automatically or manually controlled to generate audio, visual and/or tactile signals for triggering positive and aversive post-hypnotic suggestions in the subject. The apparatus and method are intended for use with subjects who have undergone hypnotherapy sessions to implant positive and aversive post-hypnotic suggestions, such as the hypnotherapy treatment method disclosed in U.S. Pat. No. 5,425,699 to Speigel, the disclosure of which is hereby incorporated by reference. This method entails providing hypnotherapy treatment to the patient, by in-person therapy sessions or by pre-recorded audio-tapes or compact disks. The therapy or recordings are utilized to enable the subject to achieve a relaxed state of increased suggestability. The therapist or recording then provides therapeutic post-hypnotic suggestions to the subject. These suggestions may be either positive, such as those inducing a state of relaxation in the subject, or negative, i.e., aversive, inducing the subject to avoid certain behavior. These post-hypnotic suggestions are linked to an active signal which will later be generated when the patient is no longer in the relaxed state.

Then, at a later time when the active signal is generated by the apparatus, either automatically, as controlled by the apparatus, or manually, as controlled by the subject, the post-hypnotic suggestion is actively triggered in the patient's mind. Methods of implanting post-hypnotic suggestion through hypnotherapy treatments which are suitable for use with the present invention are well known by those of ordinary skill in the art, and thus are not described in great detail. The present invention is instead directed to an apparatus and method for producing active signals to trigger positive and/or aversive post-hypnotic suggestions in an effective manner to treat an undesirable behavior, such as to aid smoking cessation, to reduce anxiety, or to reduce overeating.

Figure 1:
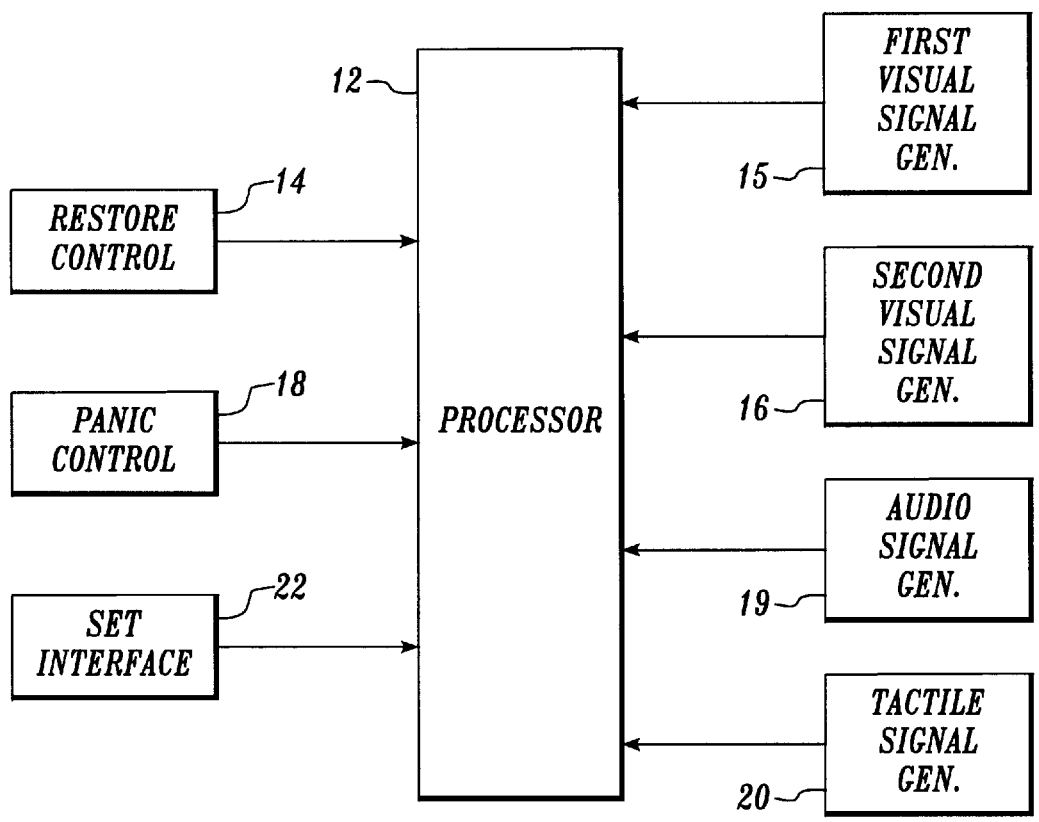
FIG. 1 is a functional block diagram of the apparatus of the present invention.

An apparatus constructed in accordance with the present invention is illustrated schematically in FIG. 1. The apparatus 10 includes a central processor 12 which controls the generation of active signals. The apparatus 10 further includes a plurality of signal generators, each of which is preferably capable of generating first active signals for triggering positive post hypnotic suggestions and second active signals for triggering aversive post-hypnotic suggestions. Specifically, the apparatus 10 includes first and second visual signal generators 15, 16, an audio signal generator 19, and a tactile signal generator 20. The apparatus further includes three manual inputs. A manual RESTORE control 14 is provided which enables the apparatus 10 to instruct the processor 12 to generate first active signals using one or more of the active signal generators 15, 16, 19, 20. Use of the control 14 overrides the normal automatic generation of first (e.g., positive) active signals. The apparatus 10 further includes a PANIC control 18 which permits the user to instruct the processor 12 to generate a second active signal using one or more of the active signal generators 15, 16, 19, 20. In the preferred embodiment, use of the control 18 is the only mechanism which results in the generation of second (e.g., aversive) active signals, although in an alternate embodiment the apparatus 10 could also be operated to normally automatically generate second active signals. The apparatus 10 further includes a set interface 22 which enables programming the processor 12 to randomly generate active signals during a predetermined time period and to set other functions of the apparatus 10, as shall be described subsequently.

Figure 2:
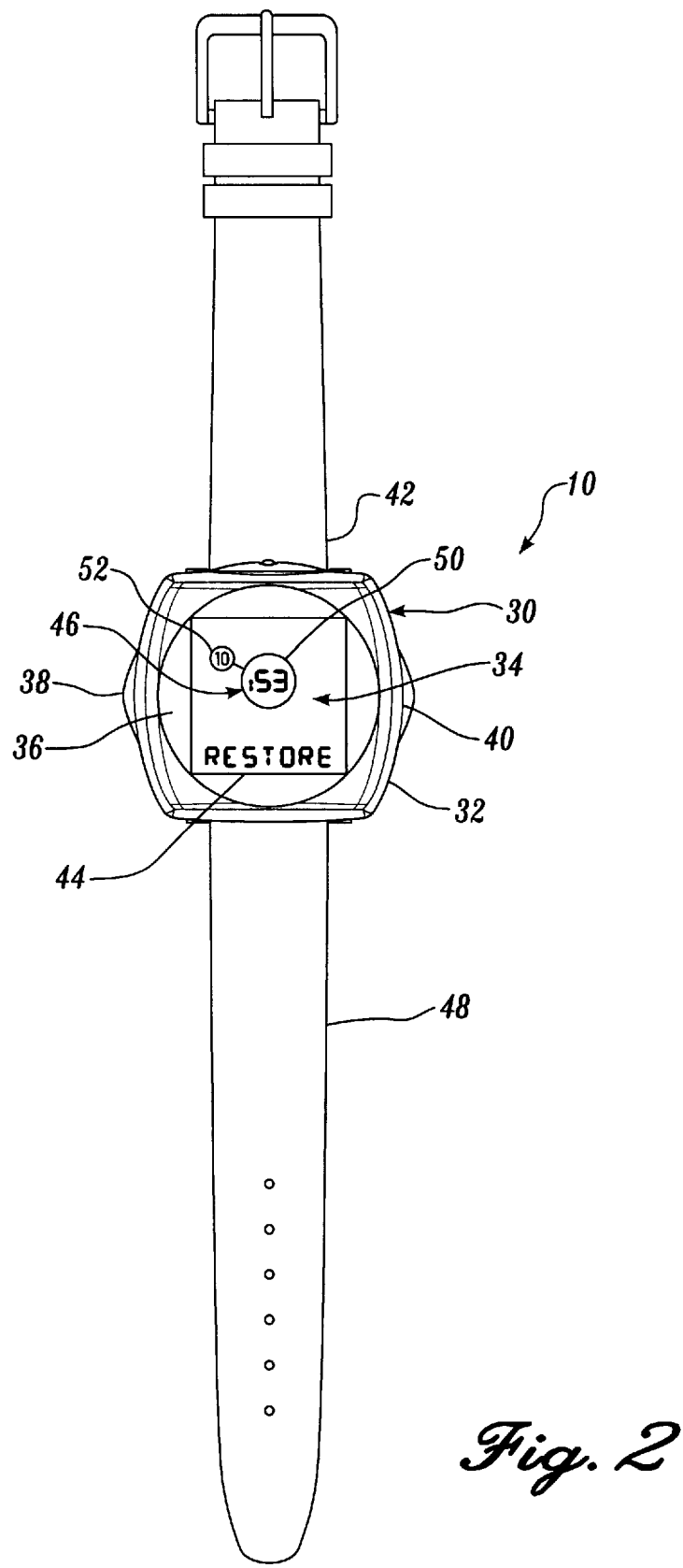
FIG. 2 is a depiction of an embodiment of a portable "wrist-watch" apparatus of the present invention.

Referring to FIG. 2, the apparatus 10 of the present invention is preferably embodied in an integrated portable device which may be carried, secured to, or worn by the subject. Preferably, the apparatus 10 is constructed as a timepiece such as a watch 30. The watch 30 includes a case 32 which contains the components of the apparatus 10, a visual display 34, and a crystal 36 which covers the visual display 34. The watch 30 further includes a manually depressable RESTORE control button 38 and a manually depressable PANIC control button 40 on opposite sides of the watch 30. The watch 30 also includes a set button 42 which enable setting the time of day and programming instructions for generating active signals.

The visual display 34 includes an alphanumeric display 44 which generates an alphanumeric active signal message, such as the word "RESTORE." The display 34 also includes a time of day display 46 for displaying the current time of day, as controlled by the processor 12. The alphanumeric display 44 and time of day display 46 may suitably be formed as liquid crystal displays. Finally, the watch 30 includes a strap 48 for securing the watch 30 to a user's wrist. The RESTORE control button 38, PANIC control button 40, set button 42, alphanumeric display 44 and time of day display 46 serve the functions of the RESTORE control 14, PANIC control 18, set interface 22, first visual signal generator 15, and second visual signal generator 16, respectively. The watch 30 also includes an audio speaker (not shown) for generating active audio signals, and a vibration generator (not shown) such as the type used in paging devices, for producing a vibratory sensation transmitted through the case to produce tactile active signals.

The watch 30 of the present invention thus is capable of producing a variety of active signals. The vibration generator is controlled by the processor to generate a first low level vibration which is intended to feel pleasant to the subject, and a second high level vibration which is intended to feel uncomfortable or unsettling to the subject. The low level vibratory signal is suitably utilized as a first active signal for the triggering of positive post-hypnotic suggestions, while the high level vibratory signal is suitably utilized as a second active signal for the triggering of aversive post-hypnotic suggestions. Likewise, the audio speaker is controlled by the processor 12 to generate a first soothing melody as a first active signal, and a second discordant tone or tune as a second active signal. The alphanumeric display 44 of the visual display 34 can be utilized to produce active signals for positive or aversive suggestions. For example, the alphanumeric display may display the word "RESTORE" to induce positive post-hypnotic suggestions. The alphanumeric display 44 may also produce instructions for use in programming the processor 12.

The time of day display 46 is useful for both displaying the actual time of day and for producing visual active signals. For example, the time of day display 46 may be programmed by the processor 12 to rapidly flash through a multitude of time of day displays to produce an active signal for triggering negative post-hypnotic suggestions. Alternatively, the time of day display 46 may be controlled by the processor 12 to generate a decrementing numeric countdown to trigger positive post-hypnotic suggestions, as will be described subsequently.

Figure 3:
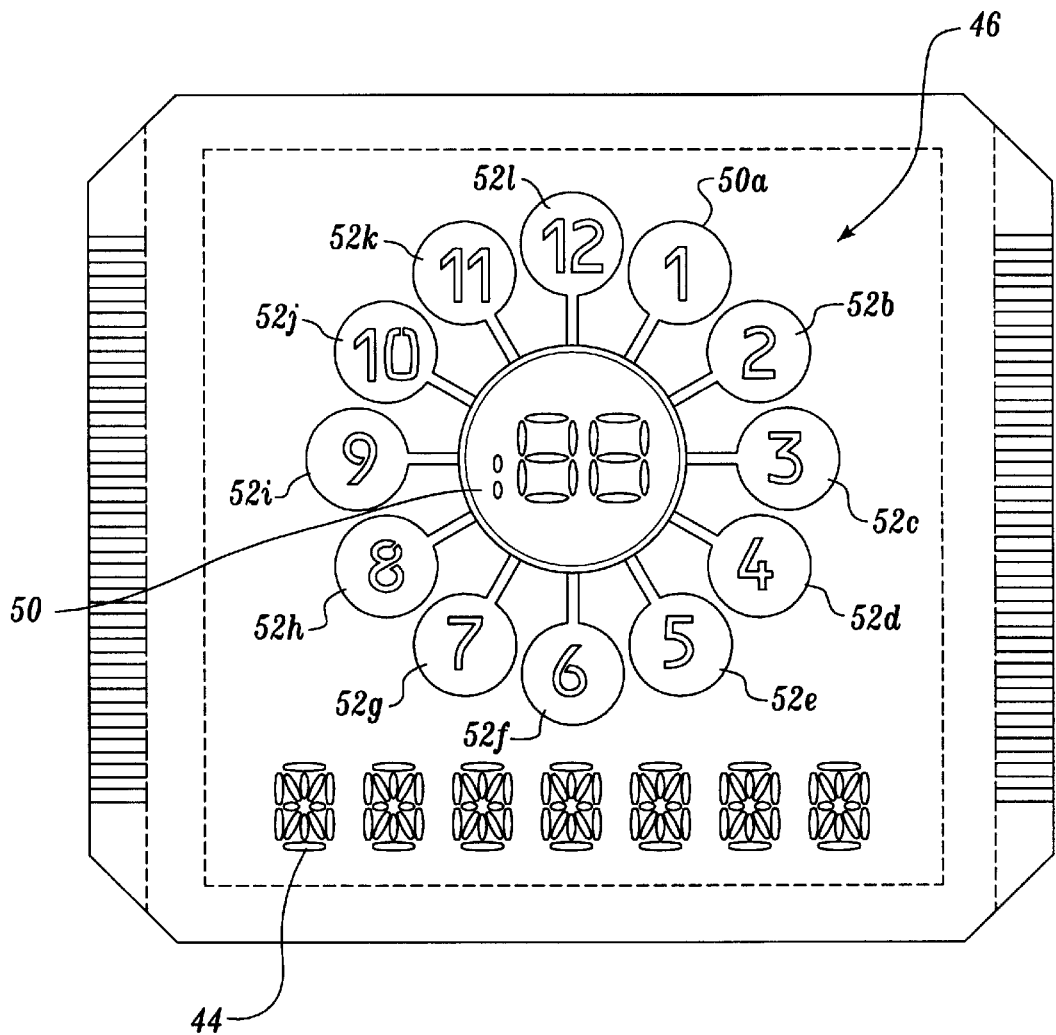
FIG. 3 is a schematic diagram of an embodiment of a display used in the wristwatch of FIG. 2.

Referring to FIGS. 2 and 3, the time of day display 46 included in the watch 30 is configured with a minute display portion 50 and an hour display portion 52. The minute portion display 50 is configured as a circular icon in which two-digit minute numerals are presented following a colon. The hour display portion 52 is configured as a smaller circular icon and is positioned radially offset from the minute display portion 50, and is connected by a spoke-like extension. The hour display portion 52 includes a single or double digit hour numeral. Referring to FIG. 3, the hour display portion 52 is generated by supplying illuminating power to one of twelve hour display stations 52a–52l. These stations are arranged radially about the minute display portion 50. As the time of day passes, the hour display stations 52a, 52b, 52c . . . are sequentially powered and activated on the display 34 to provide the appearance of the hour display 52 revolving about the minute display 50. In FIG. 2, the hour display station 52j is activated.

While providing a pleasing manner in which to display the time of day, the time of day display 46 also can be used for producing active signals. Thus, as noted above, for a positive active display, the hour display stations 52a–52i may be sequentially activated in descending order. Thus, for example, upon the start of the signal, display station 52j may be initially activated, followed in steady succession at one-second intervals by activation alternately of station 52i, 52h, 52g . . . . Thus, a radial spoke-like decrementing numeric countdown display is generated. For a negative active signal, the hour display stations 52 may be randomly momentarily activated to produce a discordant, rapidly changing display.

Usage of the watch 30 in the practice of the present invention shall now be described. In the preferred embodiment, the watch 30 is part of a behavior modification system which also includes a prerecorded audio tape or compact disc (not shown) which is used to deliver specific therapeutic sessions designed for treating undesired habits such as smoking or overeating. Those skilled in the art will readily recognize that alternative means of presenting therapeutic sessions, including live therapists, are within the scope of the present invention. The typical compact disc ("CD") of the preferred embodiment will include three tracks, identified as CDTRK 1, CDTRK 2, and CDTRK 3. CDTRK 1 will typically contain introductory information and general instructions for using the apparatus.

CDTRK 2 contains a program referred to as the RESTORE program, which is typically about twenty minutes long, including instructions and other messages for the subject. By way of nonlimiting example, when CDTRK 2 is played on a standard compact disc player (not shown), the subject will hear instructions such as: "Place the watch on your wrist. Find a quiet place and a comfortable position such as an overstuffed chair. Make sure it is comfortable for you. Make sure no one will disturb you so you can have twenty minutes of undisturbed quiet. Allow your body to settle into your seat. Allow yourself to listen only to the sounds of my voice . . . ."

After the subject has been placed in a relaxed state, CDTRK 2 will instruct the subject: "Press the left button on the watch. Feel the pleasant vibration from the watch. Listen to the pleasant melody. The vibration and melody will remind you to look at the watch. See the word 'RESTORE' rhythmically flashing on the display. When you feel this vibration or hear the melody, you will become relaxed as you are now . . . ." These relaxing post-hypnotic suggestions are referred to as the "Positive RESTORE Triggers."

CDTRK 2 also contains "Aversive PANIC Triggers" which elicit aversive post-hypnotic suggestions in the subject. These are implanted in the subject through instruction such as: "Press the right button. Feel the irritating vibration from the watch. Listen to the harsh, unpleasant noise. The vibration and noise will remind you to look at the watch. See the word 'PANIC' blinking on the display. When you feel this vibration or hear the noise, the taste of a cigarette will become foul in your mouth, the thought of lighting the cigarette makes you nauseous. Whenever you feel the urge to smoke, you will remember to press the right button on the watch."

CDTRK 3 is a "booster" program, usually about five minutes in length, wich is to be played at the end of the subject's day. It contains such messages as: "Good Job!", "Give yourself a pat on the back!", or other such motivational statements.

Differing recordings are provided for specific behaviors to be treated, such as smoking or overeating. A subject who has listened to and been conditioned by the therapy contained on CDTRK 2 or by a live therapist utilizes the watch 30 of the present invention to trigger implanted post-hypnotic suggestions to treat the behavioral problem. Referring again to FIG. 1, the processor 12 included within the watch 30 controls the overall operation of the watch. It includes programming for generating positive RESTORE triggers, and aversive PANIC triggers, which preferably include tactile, visual, and audio active signals that are generated by the active signal generators 15, 16, 19, 20. Additionally, the processor 12 includes programming to accept data from the set interface 22 representing a time period, such as a subject's work day, and programs the watch 30 to randomly activate the positive RESTORE triggers a predetermined number of times (e.g., five) during the indicated work day. When the apparatus is generating positive RESTORE triggers, it is referred to as being in the "RESTORE" mode. The random activations of the positive active signals trigger positive post-hypnotic suggestions in the subject, thereby reinforcing the behavior-modifying hypnotherapy.

Additionally, the apparatus is provided with the RESTORE control 14, in the form of button 38, which causes the apparatus to immediately enter the RESTORE mode when depressed, and the PANIC control 18, in the form of button 40, which causes the apparatus to enter a "PANIC" mode, during which aversive PANIC triggers are generated.

Figure 4A:
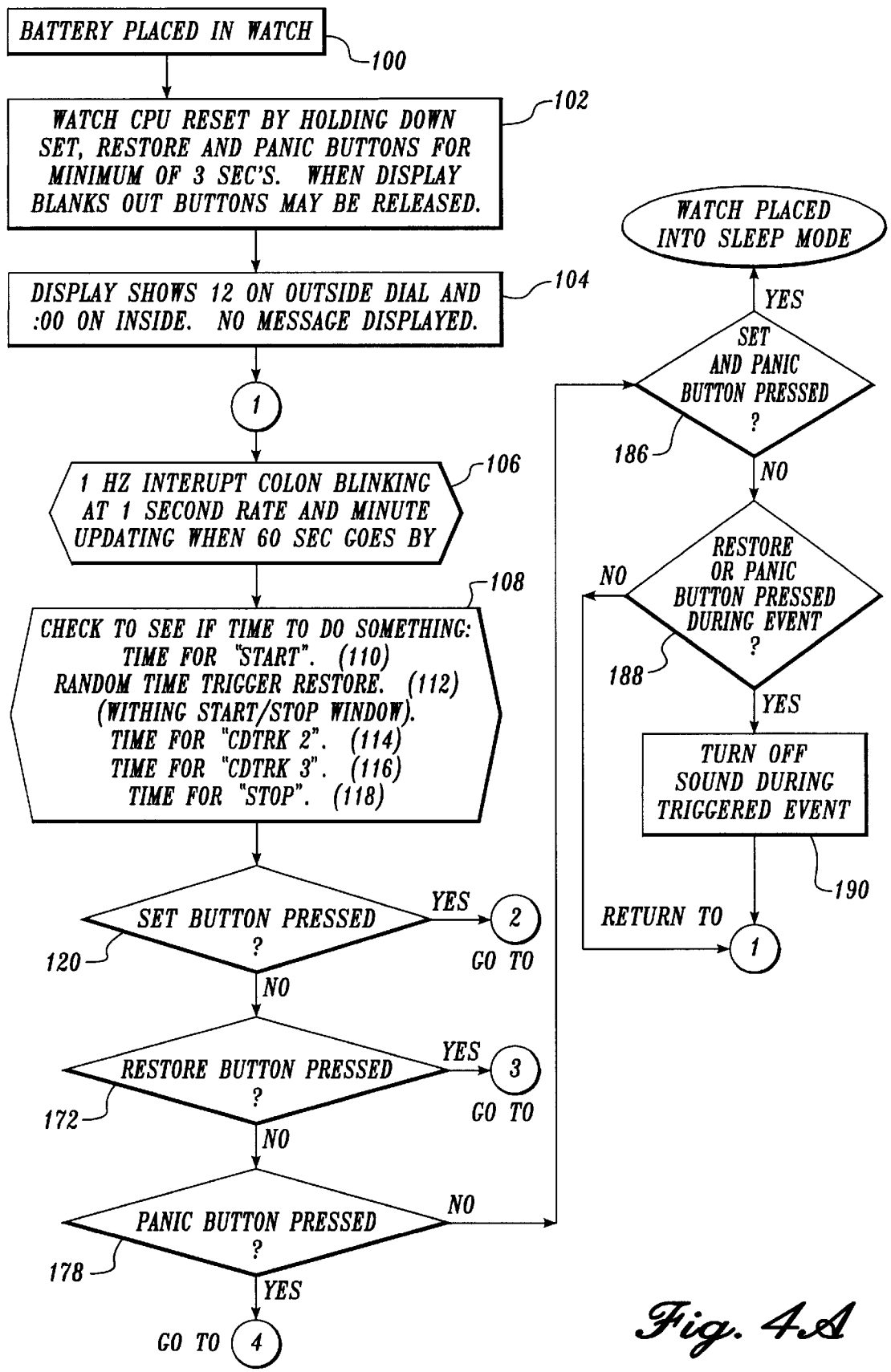
FIGS. 4A–4D provide a flowchart representing a mode of operation of the apparatus of FIG. 2 according to the present invention.
Figure 4B:
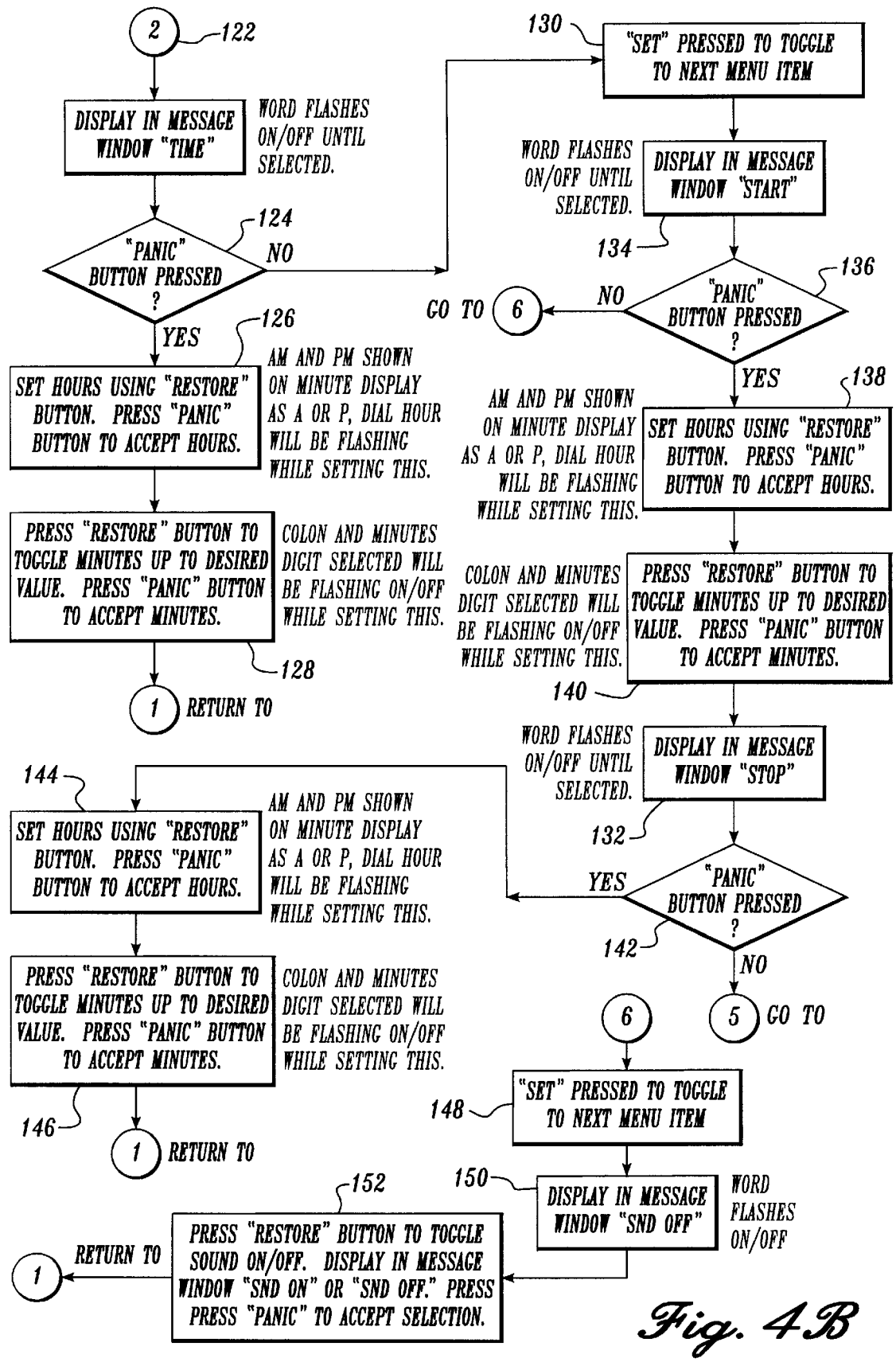
Figure 4C:
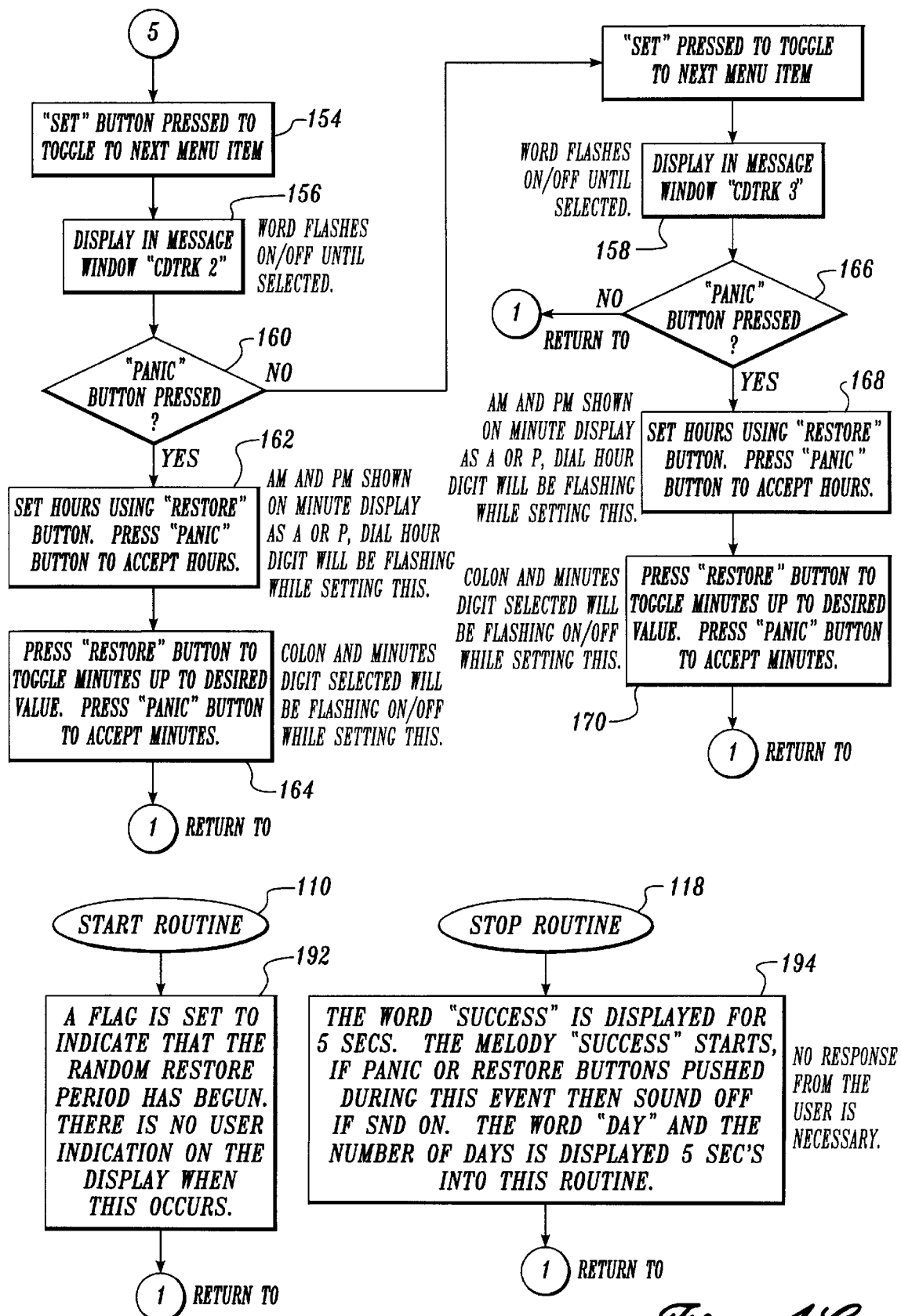

A preferred method of operating the watch 30 is illustrated in more detail in the program flow charts of FIGS. 4A through 4D, which control operation of the processor 12. Referring to FIG. 4A, operation of the watch is initiated by placing a battery into the watch (100). The watch 30 is then reset in the same manner as for a conventional watch (102). At this point the time of day display 46 displays the time 12:00 (104) and the colon in the minute display portion 50 blinks at a one-second rate (106). This is the initial block (106) of the main routine. The processor 12 then determines whether one or more subroutines need to be executed (108). These subroutines are referred to as the "START" routine (110), a "positive trigger RESTORE" routine (112), a "CDTRK 2" routine (114), a "CDTRK 3" routine (116), and the "STOP" routine (118). Each of these subroutines will be described subsequently.

If none of the subroutines checked for at block 108 are activated, the processor 12 then determines whether the set interface 22 button has been depressed. If so, the "time of day set" routine (122, see FIG. 4B) is initiated. If the PANIC control 18 button is depressed (124), the time of day can then be entered by pressing the RESTORE control 14 button and PANIC control 18 button (126, 128). At this point, the program returns to initial block 106 in the main routine.

Referring again to FIG. 4B, if in the time of day set routine 122 the PANIC control 18 button is not initially depressed, the program advances to the "set START time" routine (130, FIG. 4B). The set START time routine and the subsequently executed "set STOP time" routine (132) enable the subject to enter the beginning and end times during the day which determine a predetermined period in which the watch 30 is to randomly enter the RESTORE mode to generate positive active triggers. These START and STOP times may, for example, correspond to the beginning and end of the user's work day, so that the positive RESTORE triggers are generated randomly during the work day to inhibit undesirable behavior.

Thus, the program passes through the set START time routine 130 to enable the subject to utilize the RESTORE control button 14 and PANIC control button 18 to set the random period START time and random period STOP time. Initially, the alphanumeric display 44 of the watch 30 displays a message "START" (134). The subject then depresses the PANIC control button 18 (136) to continue with setting the START time and utilizes the RESTORE and PANIC control buttons 14, 18 to enter the START time (138, 140). The program then continues to the set STOP time routine 132, and if the user again depresses the PANIC control 18 button (142), the STOP time can be set using the RESTORE and PANIC control 14, 18 buttons (144, 146). The program then returns to the initial block 106.

While executing the set START time routine 130, the subject has the opportunity to selectively deactivate the audio triggers generated by the watch 30. At block 136 (FIG. 4B), if the PANIC control button 18 is not depressed, the program advances to the "sound off routine" (148, FIG. 4B). The various buttons on the watch 30 can then be activated to selectively disable the audio signals, in which event the alphanumeric display 44 displays "SND OFF", or to enable the audio signal, in which event "SND ON" is displayed. At the termination of the sound off routine (148, 150, 152), the program returns to initial block 106.

While executing the set STOP time routine 132, the subject also has the opportunity to set the time for the watch to automatically enter into a "CDTRK 2" mode or a "CDTRK 3" mode in which the watch 30 is activated to remind the subject to listen to the second or third track of the therapeutic compact disk or audio tape for reinforcement. Thus, at block 142 in the set STOP time routine 132 (FIG. 4B), if the PANIC control 18 button is not depressed, the program advances to block 154 (FIG. 4C) to set the time of day at which the watch 30 is to enter the CDTRK 2 mode (156), during which setting the alphanumeric display 44 displays "CDTRK 2", or the time of day at which the watch 30 is to enter the CDTRK 3 mode (158), during which setting the alphanumeric display 44 displays "CDTRK 3". Setting of the time of day for CDTRK 2 and CDTRK 3 modes are completed using the RESTORE and PANIC control 14 and 18 buttons (160, 162, 164 and 166, 168, 170, respectively), in the same manner in which the START and STOP times are set, after which the program returns to initial block 106.

Returning to FIG. 4A, if the SET button is not depressed to initiate the setting of the time of day, START time, STOP time, CDTRK 2 time or CDTRK 3 time (120), the routine continues to block 172 to determine if the RESTORE control 14 button has been depressed. If the RESTORE control button has been depressed, the program advances to the RESTORE routine 112 for immediate initiation of the RESTORE mode. The user has thus manually controlled the watch to initiate the RESTORE mode in response to some need determined by the user or some external trigger. In the RESTORE routine (FIG. 4D), the message RESTORE is displayed on the alphanumeric display 44 (174). The watch simultaneously generates several positive active signals in this mode (176). The word "RESTORE" is displayed and flashes for ten seconds, the low level vibration signal is activated for ten seconds, the hour portion stations 52 of the time of day display 46 are sequentially operated in decre- menting fashion to produce a visual countdown from 10 to 1, and, if the audio signal has not been deactivated, the positive melody is sounded. After this ten-second period, in which all of the positive triggers are simultaneously generated, the subject may depress the RESTORE control 14 button to terminate the RESTORE routine. If the RESTORE control 14 button is not depressed at the end of the ten seconds, the ten second RESTORE mode will repeat two times more. At the end of the RESTORE routine, the program returns to initial block 106 (FIG. 4A).

If it is not time to start a set routine or to activate the RESTORE routine, the processor then determines whether the PANIC control 18 button is depressed (178). If depressed, the program advances to the PANIC routine (180, FIG. 4D). The message "PANIC" is displayed in the alphanumeric display 44 (182). During the PANIC mode, a plurality of negative active signals are simultaneously produced (184). The "PANIC" display flashes on and off for ten seconds, the high level vibration signal operates for ten seconds, the hour portion stations 52 of the time of day display 46 randomly and rapidly illuminate, and the discordant PANIC melody sounds unless the sound has been disabled. All these negative active signals occur concurrently during the ten second period. At the end of the PANIC mode, the program then immediately and automatically advances to the RESTORE routine 112 to initiate the RESTORE mode. Thus, the negative associations produced by the PANIC mode are always followed immediately by the positive, relaxing sensations of the RESTORE mode. At the end of the RESTORE mode, the program returns to the main routine at initial block 106.

Referring again to FIG. 4A, in the main routine depression of both the SET and PANIC buttons at the same time (186) will place the watch into a SLEEP mode. This is an optional feature that may not be preferred for some subjects. Also, if during the RESTORE or PANIC mode of operation of the watch 30, the RESTORE or PANIC control buttons 14, 18 are depressed (188), the audio signal will be deactivated during that particular event (190).

The main routine then sequences back to initial block 106. Then in block 108 of the main program routine, if the previously programmed START time of the day has been reached, a START routine (110) is initiated which sets an internal program flag (192, FIG. 4C). During this preprogrammed period of time, the processor 12 randomly initiates the RESTORE mode (112) a predetermined number of times, each random activation of the RESTORE mode being separated by a varying interval of time. In a preferred embodiment of the present invention, the RESTORE mode is manually activated five times during the preprogrammed period of time, such as during the work day. Thus, in block 108 (FIG. 4A), if it is within the START/STOP period of time window, when the processor determines that it is time for a random RESTORE mode, the program sequences to the RESTORE routine 112. At the end of the preprogrammed period of time, when the preprogrammed STOP time is reached, the program sequences to the STOP routine (118, FIG. 4C). The word "SUCCESS" is then displayed upon the alphanumeric display 44 (194). An audio melody associated with successful completion of the time period is sounded, and the alphanumeric display 44 then displays the word "DAY" and the number of days in which the watch 30 has been utilized for the therapeutic method, which is internally tracked by the processor 12. The program then returns to the main routine at initial block 106.

Figure 4D:
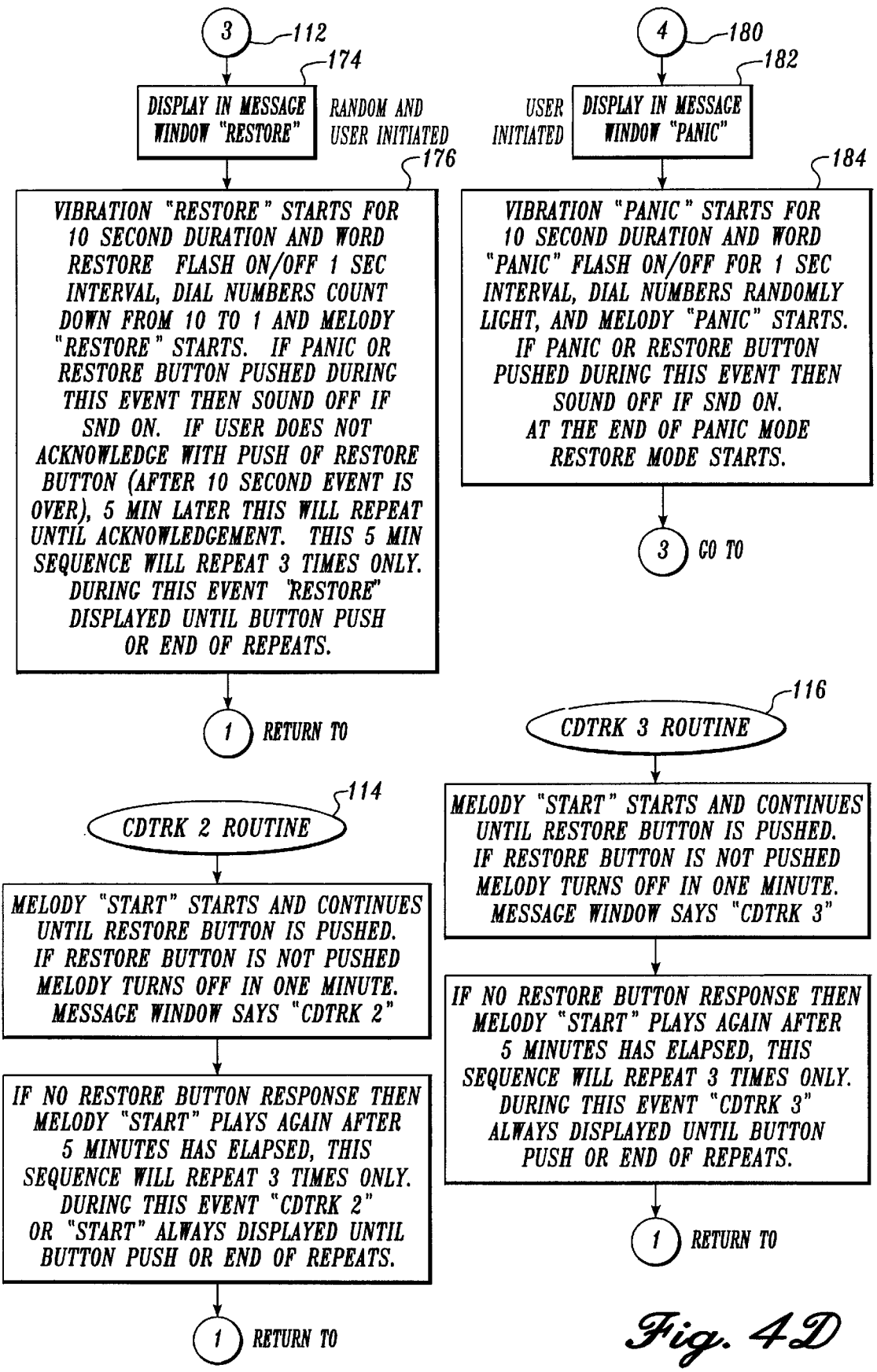

Then in block 108, if it is determined that the previously set time for initiating CDTRK2 mode has been reached, the program advances to block 114 (FIG. 4D). An audio signal associated with CDTRK 2, referred to as the "START melody" then sounds, and the message "CDTRK 2" is displayed, reminding the user that it is an appropriate time to again listen to the CDTRK 2 portion of the compact disk or audio tape to reinforce the therapeutic conditioning.

Likewise, in block 108 (FIG. 4A), if it is determined that the previously set CDTRK 3 time has been reached, the program advances to the CDTRK 3 routine (116, FIG. 4D), to play the "START" melody and display "CDTRK 3" to remind the subject that it is time to again listen to CDTRK 3 of the CD or audio tape.

In summary, the watch 30 operates to generate positive active signals triggering positive post-hypnotic suggestions at random times during a predetermined period of the day. The watch 30 may also be manually controlled to initiate the generation of positive active signals or aversive active signals, at any time during the day, by depressing the RESTORE control 14 button or PANIC control 18 button. Whenever aversive active signals are produced as a result of depressing the PANIC control 18 button, upon completion of the "PANIC" mode, the watch 30 automatically advances to the "RESTORE" mode. In each of the PANIC and RESTORE modes, the watch generates redundant active signals which may include multiple visual signals, a tactile vibratory signal, and an audio signal. The audio signal may be selectively deactivated. The watch 30 also generates preprogrammed reminders to listen to certain tracks of the accompanying CD or audio tape.

While the preferred embodiment of the watch 30 has been described above, it should be apparent that many alterations may be made within the scope of the present invention. Thus, the apparatus 30 may be configured as a differing portable device, such as a device which is strapped to the belt or carried in a purse or pocket. While the visual signals "RESTORE" and "PANIC" have been described, numerous other signals which can be implanted within the subject through the accompanying therapy may be utilized. The generation of a plurality of redundant active signals is preferred, but it should also be apparent that the apparatus could be adapted to generate only a single active signal at any given time, such as a tactile vibratory signal.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An apparatus for treating a behavioral problem of a subject who has undergone one or more hypnotherapy sessions to implant positive and aversive post-hypnotic suggestions which are to be elicited upon the occurrences of corresponding trigger events, the apparatus comprising:
   (a) a first active signal positive signal generator for triggering the positive post-hypnotic suggestions by generating a first active signal and presenting the first active signal to the subject;
   (b) a second active aversive signal generator for triggering the aversive post-hypnotic suggestions by generating a second active signal and presenting the second active signal to the subject; and
   (c) a processor programmed to control the generation of the first and second active signals, and programmed to generate the first active signal independently, and generate the second active signal independently of the first active signal.

2. The apparatus of claim 1, wherein at least one of the first active positive signal generator and the second active aversive signal generator comprises a first tactile signal generator.

3. The apparatus of claim 2, wherein the first active positive signal generator and the second active aversive signal generator comprise first and second tactile signal generators, respectively.

4. The apparatus of claim 1, wherein at least one of the first and second active signals comprises a first visual signal.

5. The apparatus of claim 4, wherein at least one of the first and second active signals comprises a plurality of visual signals.

6. The apparatus of claim 1, wherein at least one of the first active positive signal generator and the second active aversive signal generators comprises a first audio signal generator.

7. The apparatus of claim 1, wherein the first active positive signal generator and the second active aversive signal generator comprise first and second audio signal generators, respectively.

8. The apparatus of claim 1, further comprising at least one redundant active signal which may be generated in conjunction with the first or the second active signal.

9. The apparatus of claim 8, wherein the redundant active signal includes means for the subject to selectively activate or deactivate the redundant active signal.

10. The apparatus of claim 1, wherein the apparatus is portable and includes means for securing the apparatus to the subject.

11. The apparatus of claim 10, wherein the means for securing comprises a wrist band such that the apparatus may be worn on the subject's wrist.

12. The apparatus of claim 1, further comprising a visual display for displaying at least one of the first and second active signals.

13. The apparatus of claim 12, wherein the display comprises an alphanumeric display.

14. The apparatus of claim 13, wherein the alphanumeric display includes a first alphanumeric message which is displayed in conjunction with the generation of one of the first and second active signals.

15. The apparatus of claim 14, wherein the alphanumeric display includes a second alphanumeric message which is displayed in conjunction with the generation of the other of the first and second active signals.

16. The apparatus of claim 14, wherein the display further comprises a graphical display that is displayed in conjunction with the generation of the first alphanumeric message.

17. The apparatus of claim 12, further comprising a time of day display, wherein the time of day display is modified by the processor in conjunction with the generation of one of the first and second active signals.

18. The apparatus of claim 17, wherein the time of day display includes means for producing a decrementing numeric count down in response to the time of day display being modified by the processor.

19. The apparatus of claim 1, further comprising a first manual control selectively activatable by the subject to generate one of the first and second active signals.

20. The apparatus of claim 19, further comprising a second manual control selectively activatable by the subject to generate the other of the first and second active signals.

21. The apparatus of claim 1, wherein the processor further includes means for causing the first active signal to be automatically generated a predetermined time period after the second active signal is generated.

22. The apparatus of claim 1, further comprising means for entering user data.

23. The apparatus of claim 22, wherein the user data comprises data indicating a time period.

24. The apparatus of claim 23, wherein the processor further comprises means for controlling the apparatus to automatically generate the first active signal a predetermined number of times at random intervals during the indicated time period.

25. The apparatus of claim 1, further comprising:
    (a) means for entering data; and
    (b) said processor is programmed to control the first active positive signal generator to automatically generate the first active signal at random time intervals according to entered data.

26. The apparatus of claim 25, wherein the entered data comprises a time period during which the first signal generator is controlled to automatically generate the first active signal at a predetermined number of random time intervals.

27. An apparatus for treating a behavioral problem of a subject who has undergone one or more hypnotherapy sessions to implant positive and/or aversive post-hypnotic suggestions which are to be elicited upon the occurrences of corresponding trigger events, the apparatus comprising:
    (a) a first active signal generator for triggering one of a positive and an aversive post-hypnotic suggestion by generating a first active signal and presenting the first active signal to the subject;
    (b) a second active signal generator for triggering the other of a positive and an aversive post-hypnotic suggestion by generating a second active signal and presenting the second active signal to the subject;
    (c) a processor programmed to control the generation of the first active signal independently of the generation of the second active signal and the generation of the second active signal independently of the generation of the first active signal, the processor further programmed to automatically control the generation of an active signal for triggering a positive post-hypnotic suggestion a predetermined time period after generation of an active signal for triggering an aversive post-hypnotic suggestion; and
    (d) a first manual control selectively activatable by the subject to generate the first active signal.

28. The apparatus of claim 27, further comprising a second manual control selectively activatable by the subject to generate the second active signal.

29. A method for treating a behavioral problem of a subject comprising the steps of:
    (a) implanting a positive post-hypnotic suggestion in the subject, the positive post-hypnotic suggestion to be elicited upon the occurrence of a corresponding positive trigger event;
    (b) implanting an aversive post-hypnotic suggestion in the subject, the aversive post-hypnotic suggestion to be elicited upon the occurrence of a corresponding aversive trigger event;
    (c) providing a portable active signal generating device to the subject;
    (d) generating a first active positive signal with the device to trigger the positive post-hypnotic suggestion in the subject; and
    (e) generating a second active aversive signal with the device to trigger the aversive post-hypnotic suggestions in the subject; wherein the steps of generating a first active positive signal and generating a second active aversive signal are mutually independent.

* * * * *

UNITED STATES PATENT AND TRADEMARK OFFICE
CERTIFICATE OF CORRECTION

PATENT NO. : 5,823,932
DATED : October 20, 1998
INVENTOR(S) : R.B. Speigel

It is certified that error appears in the above-indentified patent and that said Letters Patent is hereby corrected as shown below:

On the title page,

| COLUMN | LINE | |
|---|---|---|
| [56] Pg. 1, col. 1 | Refs. Cited (U.S. Pats.) | after "Speigel" insert --4,227,516 10/1980 Meland et al. 600/026 5,599,274 02/1997 Widjaja et al. 600/027-- |
| [57] Pg. 1, col. 2 | Abstract (line 3 of text) | "posthypnotic" should read --post-hypnotic-- |
| [57] Pg. 1, col. 2 | Abstract (line 9 of text) | "posthypnotic" should read --post-hypnotic-- |
| 11 (Claim 1, | 55 line 6) | after "active" delete "signal" |
| 12 (Claim 6, | 16 line 3) | "generators" should read --generator-- |

Signed and Sealed this

Fourth Day of May, 1999

Attest:

Q. TODD DICKINSON

*Attesting Officer*       *Acting Commissioner of Patents and Trademarks*